US008247548B2

(12) United States Patent
Yang et al.

(10) Patent No.: US 8,247,548 B2
(45) Date of Patent: Aug. 21, 2012

(54) ISOELECTRONIC HETEROANALOGUES OF PCBM AND $C_{60}$ FOR N-BRIDGED PCBMS FOR ORGANIC ELECTRONIC MATERIAL

(75) Inventors: Changduk Yang, Goleta, CA (US); Fred Wudl, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 450 days.

(21) Appl. No.: 12/603,409

(22) Filed: Oct. 21, 2009

(65) Prior Publication Data
US 2010/0139773 A1    Jun. 10, 2010

Related U.S. Application Data

(60) Provisional application No. 61/107,169, filed on Oct. 21, 2008.

(51) Int. Cl.
*C07D 223/14* (2006.01)
*H01L 27/00* (2006.01)
(52) U.S. Cl. ............. 540/576; 257/69; 313/498; 560/19
(58) Field of Classification Search .................. 540/576; 257/69; 313/498; 560/19
See application file for complete search history.

(56) References Cited

OTHER PUBLICATIONS

Thilgen, C.; Diederich, F. Chem. Rev. 2006, 106, 5049.
Janssen, R. A. J.; Hummelen, J. C.; Wudl, F. J. Am. Chem. Soc. 1995, 117, 544.
Hummelen, J. C.; Knight, B. W.; Lepeq, F.; Wudl, F.; Yao, J.; Wilkins, C. L. J. Org. Chem. 1995, 60, 532.
Maggini, M.; Scorrano, G.; Bianco, A.; Toniolo, C.; Sijbesma, R. P.; Wudl, F.; Prato, M. J. Chem. Soc., Chem. Commun. 1994, 305.
Taylor, R.; Walton, D. R. M. Nature 1993, 363, 685.
Rubin, Y.; Khan, S.; Freedberg, D. I.; Yeretzian, C. J. Am. Chem. Soc. 1993, 115, 344.
Prato, M.; Suzuki, T.; Foroudian, H.; Li, Q.; Khemani, K.; Wudl, F.; Leonetti, J.; Little, R. D.; White, T.; Rickborn, B.; Yamago, S.; Nakamura, E. J. Am. Chem. Soc. 1993, 115, 1594.
Meier, M. S.; Poplawska, M. J. Org. Chem. 1993, 58, 4524.
Komatsu, K.; Kagayama, A.; Murata, Y.; Sugita, N.; Kobayashi, K.; Nagase, S.; Wan, T. S. M. Chem. Lett. 1993, 2163.
Wudl, F. Acc. Chem. Res. 1992, 25, 157.
Vasella, A.; Uhlmann, P.; Waldraff, C. A. A.; Diederich, F.; Thilgen, C. Angew. Chem., Int. Ed. Engl. 1992, 31, 1388.
Paolucci, F.; Marcaccio, M.; Roffia, S.; Orlandi, G.; Zerbetto, F.; Prato, M.; Maggini, M.; Scorrano, G. J. Am. Chem. Soc. 1995, 117, 6572.
Eiermann, M.; Wudl, F.; Prato, M.; Maggini, M. J. Am. Chem. Soc. 1994, 116, 8364.
Diederich, F.; Isaacs, L.; Philp, D. Chem. Soc. Rev. 1994, 23, 243.
Cases, M.; Duran, M.; Mestres, J.; Martin, N.; Solà, M. J. Org. Chem. 2001, 66, 433.
Grösser, T.; Prato, M.; Lucchini, V.; Hirsch, A.; Wudl, F. Angew. Chem., Int. Ed. Engl. 1995, 34, 1343.
Prato, M.; Li, Q. C.; Wudl, F.; Lucchini, V. J. Am. Chem. Soc. 1993, 115, 1148.
Guldi, D. M.; Hungerbühler, H.; Carmichael, I.; Asmus, K. D.; Maggini, M. J. Phys. Chem. A 2000, 104, 8601.
Hirsch, A. In Fullerenes and Related Structures in Topics in Current Chemistry, 1999; vol. 199, p. 1.
Averdung, J.; Mattay, J. Tetrahedron 1996, 52, 5407.
Benati, L.; Leardini, R.; Minozzi, M.; Nanni, D.; Spagnolo, P.; Strazzari, S.; Zanardi, G. Org. Lett. 2002, 4, 3079.
Haddon, R. C. Science 1993, 261, 1545.
Brabec, C. J.; Cravino, A.; Meissner, D.; Sariciftci, N. S.; Fromherz, T.; Rispens, M. T.; Sanchez, L.; Hummelen, J. C. Adv. Funct. Mater. 2001, 11, 374.
Changduk Yang, et al., Functionalized Methanofullerenes Used as n-Type Materials in Bulk-Heterojunction Polymer Solar Cells and in Field-Effect Transistors, J. Am. Chem. Soc. 130(20), 6444-6450 (2008).
International Search Report and Written Opinion of the ISA for PCT/US2009/061533., Dec. 15 , 2009.
Nanjo, M., et al., Donor-Acceptor C60-Containing Polyferrocenylsilanes: Synthesis, Characterization and Applications in Photodiode Devices, Adv. Funct. Mater. (2008), 18, 470-477.
Spitsina, N., et al., Poly(2-methoxy-5-(2'-ethyl-hexyloxy)-1,4-phenylene vinylene)(MEH-PPV)/Nitrogen Containing Derivatives of Fullerene Composites: Optical Characterization and Application in Flexible Polymer Solar Cells, Journal of Low Temperature Physics, vol. 142, Nos. 3/4, Feb. 2006.

*Primary Examiner* — Charanjit Aulakh
(74) *Attorney, Agent, or Firm* — Berliner & Associates (57) ABSTRACT

N-bridged PCBMs are prepared by the cycloaddition of an organic azide to $C_{60}$. The N-bridged PCBMs are imino PCBMs, exemplified by an isomeric mixture of [5,6]-open APCBM and [6,6]-closed APCBM. An organic electronic material containing a fullerene adduct, such as an organic field effect transistor or an organic photovoltaic device, is provided containing the N-bridged PCBM as the fullerene adduct.

4 Claims, 8 Drawing Sheets

ISOELECTRONIC HETEROANALOGUES OF PCBM AND $C_{60}$ FOR N-BRIDGED PCBMS FOR ORGANIC ELECTRONIC MATERIAL

CROSS-REFERENCE TO RELATED APPLICATIONS

This application claims the benefit of Provisional Patent Application No. 61/107,169 filed on Oct. 21, 2008, which is incorporated by reference herein.

BACKGROUND

1. Field of the Invention

The invention relates to fullerene derivates and methods of making such compounds.

2. Related Art

The extraordinary electronic properties of fullerene $C_{60}$, as an n-type semiconductor with relatively high carrier mobility, have evoked continued interest to develop a wide variety of chemically modified fullerene derivatives (1-13). One of the most reliable and versatile routes to functionalization has been studied through the addition of diazo compounds to $C_{60}$ (11), resulting in two isomeric products such as [5,6]-open fulleroids and [6,6]-closed methanofullerenes (2,3). From an electronic structure point of view, the [5,6]-open isomers conserve the π-electrons of the parent $C_{60}$. However, they readily transform to the thermodynamically more stable [6,6]-closed isomers by thermal, electrochemical, pH and photochemical means (2, 3, 14-16), thus making their intrinsic properties in electronic applications difficult to assess.

It has been shown that 1,3-dipolar [3+2]cycloaddition of azides to $C_{60}$, followed by thermal extrusion of $N_2$ of the triazoline intermediate, leads to [1,6]-azafulleroids and [1,2]-aziridinofullerenes, respectively (18, 19). Depending on the nature of the substituents, the thermal $N_2$ elimination affords different ratios of the two isomeric imino adducts (21-23).

Fullerene adducts have been used in organic electronic devices such as organic photovoltaics (OPVs) and organic field effect transistors (OFETs), as described in the following patents and published patent applications, the disclosures of which are all incorporated herein by reference: a) U.S. Pat. No. 7,329,709, titled: "Photoactive materials and related compounds, devices, and methods"; b) U.S. Pat. No. 6,960,782, titled: "Electronic devices with fullerene layers"; c) U.S. Pat. Nos. 6,933,436 and 6,812,399, both titled: "Photovoltaic cell"; d) U.S. Pat. No. 5,693,977, titled: "N-channel field effect transistor including a thin film fullerene"; e) U.S. Pat. No. 5,171,373, titled: "Devices involving the photo behavior of fulleroides"; f) U.S. Patent Publication No. 20070215872, titled: "Organic semiconductor material and organic device using the same"; and g) U.S. Patent Publication No. 20040016922, titled: "Electronic devices." However, there is a continuing need to improve the electronic properties of fullerene adducts.

SUMMARY

In one aspect, a method for preparing N-bridged PCBMs is provided. As used herein, the term "N-bridged PCBM," "imino PCBM" or "APCBM" refers to analogs of [6,6]-phenyl-$C_{61}$-butyric acid methyl ester (PCBM) that are nitrogen-bridged rather than carbon-bridged to a fullerene $C_{60}$. In the term "APCBM," the "A" stands for "aza."

The method includes reacting an organic azide with $C_{60}$ by cycloaddition to produce at least one N-bridged PCBM. In embodiments of the method, the organic azide can be methyl 5-azido-5-phenylpentanoate. In embodiments of the method, including but not limited to embodiments where methyl 5-azido-5-phenylpentanoate is the organic azide, the at least one N-bridged PCBM can be an imino PCBM. In embodiments where the N-bridged PCBM is an imino PCBM, the imino PCBM can be [5,6]-open APCBM or [6,6]-closed APCBM, or the at least one N-bridged PCBM can be an isomeric mixture of [5,6]-open APCBM and [6,6]-closed APCBM.

In embodiments of the method, including but not limited to those described in the preceding paragraph, the reacting can occur under an inert atmosphere, such as in the presence of argon or nitrogen. Also, the reacting can further include extruding $N_2$ from a reaction intermediate. In addition, the method can further include purifying one or more components of the at least one N-bridged PCBM.

In another aspect, an organic electronic device comprising at least one N-bridged PCBM is provided. In embodiments of the device, the at least one N-bridged PCBM can be an imino PCBM, which in some embodiments can be [5,6]-open APCBM or [6,6]-closed APCBM. In certain embodiments of the device, the imino PCBM is [5,6]-open APCBM. In embodiments of the device, including but not limited to embodiments containing imino PCBMs and embodiments containing [5,6]-open APCBM or [6,6]-closed APCBM, the at least one N-bridged PCBM can have an electron mobility that is greater than the electron mobility of PCBM when measured under similar conditions.

In embodiments of the device, including but not limited to those described in the preceding paragraph, the organic electronic device can be an organic field effect transistor or organic photovoltaic device.

In a further aspect, an imino PCBM is provided. The imino PCBM is can be [5,6]-open APCBM, [6,6]-closed APCBM, or an isomeric mixture thereof.

BRIEF DESCRIPTION OF THE DRAWINGS

For a more complete understanding of the present invention, reference is now made to the following descriptions taken in conjunction with the accompanying drawing, in which.

DETAILED DESCRIPTION

Figure 1:
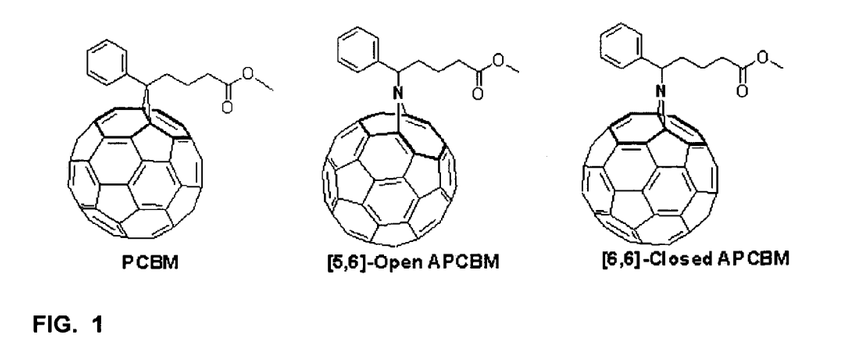
FIG. 1 is a diagram showing the structures of PCBM, [5,6]-open APCBM, and [6,6]-closed APCBM.

To prepare isomeric fullerenes, a method is provided that comprises the addition of an organic azide to $C_{60}$ to form an N-bridged PCBM, which can be useful as adducts in organic electronic material such OPVs, OFETs, and photodetectors. Some embodiments of the method include the one-pot preparation of two isomeric imino PCBMs, namely [5,6]-open azafulleroid ([5,6]-open APCBM) and [6,6]-closed aziridinofullerene ([6,6]-closed APCBM). The structure of these imino PCBMs is shown in FIG. 1 along with PCBM. In these embodiments of the method, the [5,6]-open APCBM and the [6,6]-closed APCBM are prepared by cycloaddition of an organic azide to $C_{60}$. These "azalogs" enable the study of the effects of the bridge atom in a fullerene cage, i.e. $C_{60}$-like (5,6-open) versus PCBM-like (6,6-closed), as a function of the changed fullerene's $\pi$-system. The "azalogs" also enable one to access the influence of the nitrogen atom, instead of bridge carbon, in the fullerene framework.

In one embodiment, the preparation of two imino PCBMs ([5,6]-open APCBM and [6,6]-closed APCBM), is performed by thermal reaction of an organic azide, methyl 5-azido-5-phenylpentanoate (24), with $C_{60}$ followed by in situ thermal $N_2$ extrusion, as shown in the following scheme:

[5,6]-Open APCBM

[6,6]-Closed APCBM

Organic azides that are derivatives of methyl 5-azido-5-phenylpentanoate can also be used to prepare imino PCBMs, including but not limited to derivatives such as: methyl-5-azido-5-thienylpentanoate; methyl-5-azido-5-naphthylpentanoate; methyl-5-azido-5-pyranylpentanoate; propyl-5-azido-5-phenylpentanoate; butylyl-5-azido-5-phenylpentanoate; pentyl-5-azido-5-phenylpentanoate; hexyl-5-azido-5-phenylpentanoate; heptyl-5-azido-5-phenylpentanoate, and more generally R-5-azido-5-phenylpentanoate, where R is octyl, nonyl, decyl, or dodecyl; methyl-5-azido-5-methoxyphenylpentanoate; and methyl-5-azido-5-trimethoxyphenylpentanoate.

In embodiments of the method, an organic azide can be mixed with $C_{60}$ and a solvent such as o-dichlorobenzene (o-DCB) and stirred under an inert gas such as argon. The solution can then be heated and allowed to further react. After concentration, the mixture can be run through a silica gel column to fractionate the imino PCBM products.

To prepare organic electronic devices, an imino PCBM-containing active layer can be deposited on a substrate or electrode layer by spin-coating. Fabrication processes can be carried out under an inert atmosphere, such as under $N_2$.

The present invention may be better understood by referring to the accompanying examples, which are intended for illustration purposes only and should not in any sense be construed as limiting the scope of the invention as defined in the claims appended hereto.

Example 1

The reaction of azides with $C_{60}$ was investigated for the following reasons: (i) possible increased degree of stabilization of [5,6]-open vs. [6,6]-closed isomers (17-19); and (ii) potential influence of the nitrogen heteroatom of iminofullerenes on the fullerene cage's electronic properties (20), possibly tuning the device performance. This is important since it enables the study of electronic device performance in comparison with two isomeric configurations, that is, hexagon-pentagon ($C_{60}$-like) versus hexagon-hexagon junction (PCBM-like), as a function of the perturbation of the fullerenes' $\pi$-system. As far as known, there exist no examples of the performance in the electronic applications for evaluation between methanofullerene and iminofullerene $C_{60}$ adducts.

Example 2

Materials and Methods

All solvents were purified and freshly distilled prior to use according to literature procedures. The synthesis of methyl 5-azido-5-phenylpentanoate was adapted from literature procedures (24). Commercially available materials were used as received unless noted. $^1$H and $^{13}$C NMR spectra were recorded on a Varian Unity Inova 500 MHz spectrometer and referenced to the solvent peak. Mass spectrometry and elemental analyses were performed by UC Santa Barbara Mass spectrometry Lab and elemental analysis center. The electrochemical measurements were carried out in o-DCB solution containing 0.1 M Bu$_4$NClO$_4$ as the supporting electrolyte, with Ag/AgCl as reference electrode and a platinum wire as a counter electrode, respectively, and an internal ferrocene/ferrocenium standard.

OFET Device Preparation and Measurement

Figure 3:
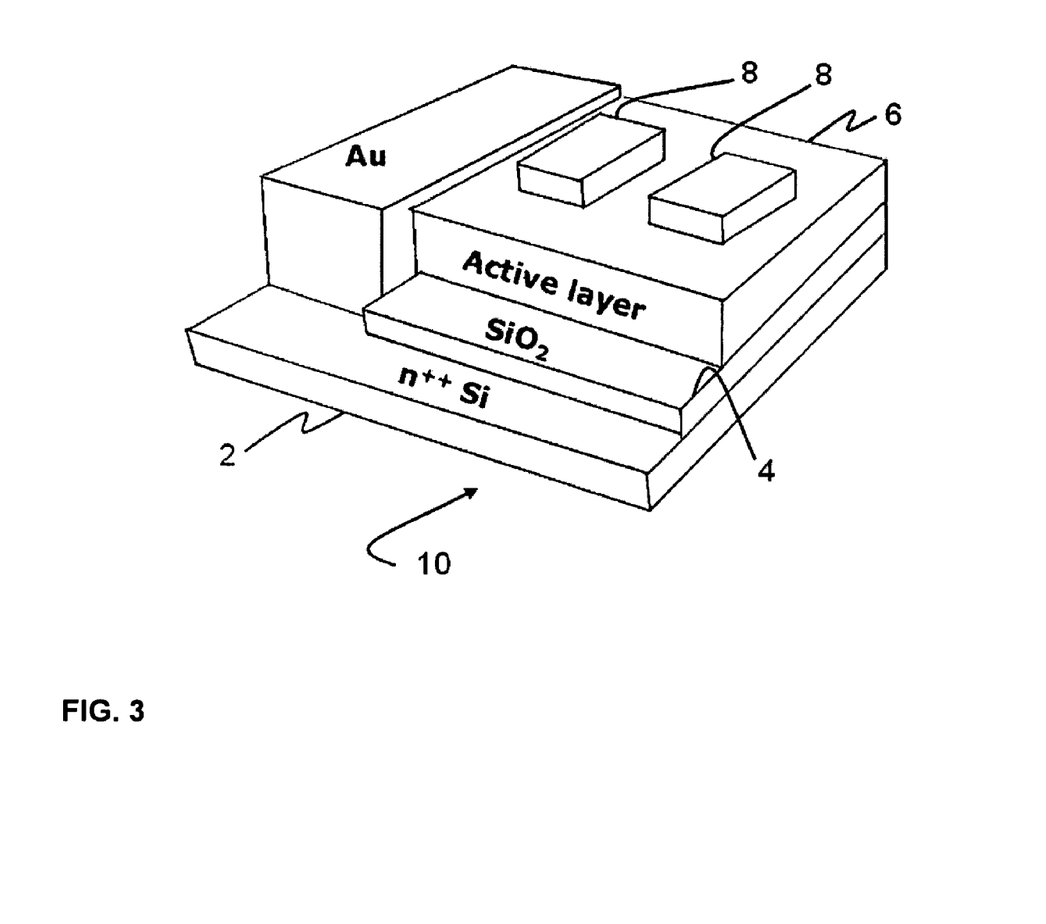
FIG. 3 is a schematic diagram of an n-type OFET structure (L=50 μm, W=1.5 mm)

Referring to FIG. 3, all n-type OFETs were fabricated on heavily doped n-type silicon (Si) wafers 2 covered with a thermally grown silicon oxide (SiO$_2$) layer 4 with thickness of 200 nm. The doped Si wafer acts as a gate electrode and the SiO$_2$ layer functions as the gate insulator. The active layer 6 was deposited by spin-coating at 2500 rpm. All solutions were prepared at 1 wt. % concentration in chloroform. The thickness of the deposited films was about 60 nm. Prior to deposition of source-drain electrodes, the films were dried on a hot plate stabilized at 80° C. for 30 minutes. All fabrication processes were carried out in a glove box filled with N$_2$. Source and drain electrodes 8 using Ca/Al double layer were deposited by thermal evaporation using a shadow mask. The thickness of source and drain electrodes was total 80 nm (Ca: 30 nm, Al: 50 nm). The Al additional metal layer was deposited as passivation metal layer to prevent fast degradation of Ca electrodes. Channel length (L) and channel width (W) were 50 μm and 1.5 mm, respectively. Referring to FIG. 3, each optical electronic device 10 was made in the top contact geometry. Electrical characterization was performed using a Keithley semiconductor parametric analyzer (Keithley 4200) under N$_2$ atmosphere. The electron mobility (μ) was determined using the following equation in the saturation regime:

$$I_{ds}=(WC_i/2L)\times\mu\times(V_{gs}-V_T)^2,$$

where $C_i$ is the capacitance per unit area of the SiO$_2$ dielectric ($C_i$=15 nF/cm$^2$), $V_T$ is the threshold voltage.

Preparation of [5,6]-Open Azafulleroid ([5,6]-Open APCBM) and [6,6]-Closed Aziridinofullerene ([6,6]-Closed APCBM)

A mixture of 5-azido-5-phenylpentanoate (0.7 g 3.0 mmol), C$_{60}$ (2.16 g, 3.0 mmol) and o-DCB (150 mL) was placed in a round bottom flask under argon and stirred at RT for 15 min. The homogeneous mixture was stirred at 60° C. under argon overnight. The solution was heated at 135° C. and allowed to continue overnight again. The resulting mixture was concentrated in vacuo to 100 mL and pre-eluted with chlorobenzene (100 mL) and then toluene on SiO$_2$/toluene, 40×10 cm. The first fraction, containing unreacted C$_{60}$, was collected (1.35 g, 63%). After this, the fraction containing [5,6]-open APCBM (R$_f$=0.57) was collected. The solution was concentrated in vacuo, redissolved in a minimal amount of toluene and transferred to a centrifuge tube. The product was precipitated with MeOH, centrifuged and decanted. The product was treated with MeOH several times in the same manner. Isolated yield=470 mg (45% based on consumed C$_{60}$) as a brown solid. $^1$H NMR (CS$_2$/CDCl$_3$ ⅓, 500 MHz): δ ppm 7.68 (d, J=7.10 Hz, 2H), 7.43 (t, J=7.57 Hz, 2H), 7.34 (t, J=7.57 Hz, 1H), 5.20 (dd, J=9.33, 3.39 Hz, 1H), 3.64 (s, 3H), 2.41-2.23 (m, 4H) 1.69-1.62 (m, 2H), $^{13}$C NMR (CS$_2$/CDCl$_3$ ⅓, 125.70 MHz): δ 172.13, 147.03, 144.71, 144.57, 144.40, 144.00, 143.87, 143.75, 143.70, 143.61, 143.49, 143.21, 143.06, 143.04, 142.84, 142.77, 142.68, 142.41, 142.35, 142.30, 142.26, 134.07, 141.94, 141.02, 140.95, 140.56, 140.51, 140.31, 139.74, 139.04, 139.01, 138.96, 138.32, 138.11, 138.03, 137.22, 136.33, 136.25, 136.15, 136.03, 135.95, 133.78, 133.38, 128.50, 128.07, 127.79, 64.10, 50.80, 35.78, 33.38, 20.47, FABMS (NBA) m/z: 926 ((M+H)$^+$.). Elemental analysis: Calculated for C$_{72}$H$_{15}$NO$_2$: C, 93.40; H, 1.63; N, 1.51; O, 3.46. Found: C, 93.29; H, 2.10; N, 1.70.

Upon ongoing elution, [6,6]-closed APCBM as a second fraction (R$_f$=0.53) was collected and further purified by triple preparative column chromatography (toluene/CS$_2$=1:1). Workup as described above (using MeOH). Isolated yield=50 mg (4.8% based on consumed C$_{60}$) as a dark-reddish solid. $^1$H NMR (CS$_2$/CDCl$_3$ ⅓, 500 MHz): δ ppm 7.75 (d, J=7.02 Hz, 2H), 7.48 (t, J=7.67 Hz, 2H), 7.40 (t, J=7.67 Hz, 1H), 4.56 (dd, J=7.66, 5.42 Hz, 1H), 3.66 (s, 3H), 2.51-2.41 (m, 4H) 1.97-1.89 (m, 2H), $^{13}$C NMR (CS$_2$/CDCl$_3$ ⅓, 125.70 MHz): δ 172.62, 144.76, 144.68, 144.26, 144.18, 144.07, 143.33, 142.61, 142.44, 141.85, 141.67, 140.31, 139.31, 128.48, 127.81, 127.64, 63.54, 50.97, 36.11, 33.63, 21.16, FABMS (NBA) m/z: 926 ((M+H)$^+$.). Elemental analysis: Calculated for C$_{72}$H$_{15}$NO$_2$: C, 93.40; H, 1.63; N, 1.51; O, 3.46. Found: C, 93.54; H, 1.86; N, 1.71.

Results

Figure 4:
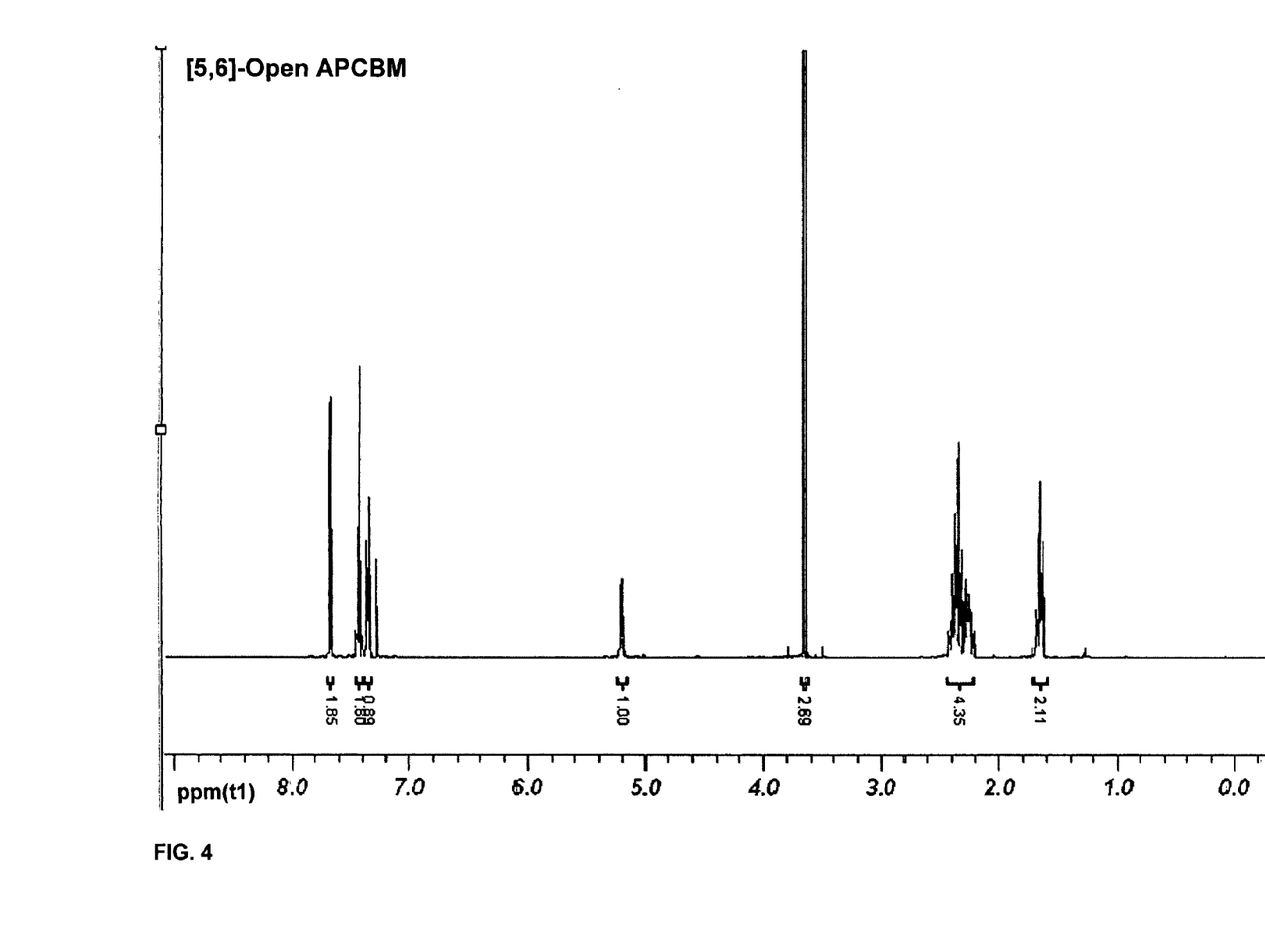
FIG. 4 is a $^1$H NMR spectrum of [5,6]-open APCBM.
Figure 5:
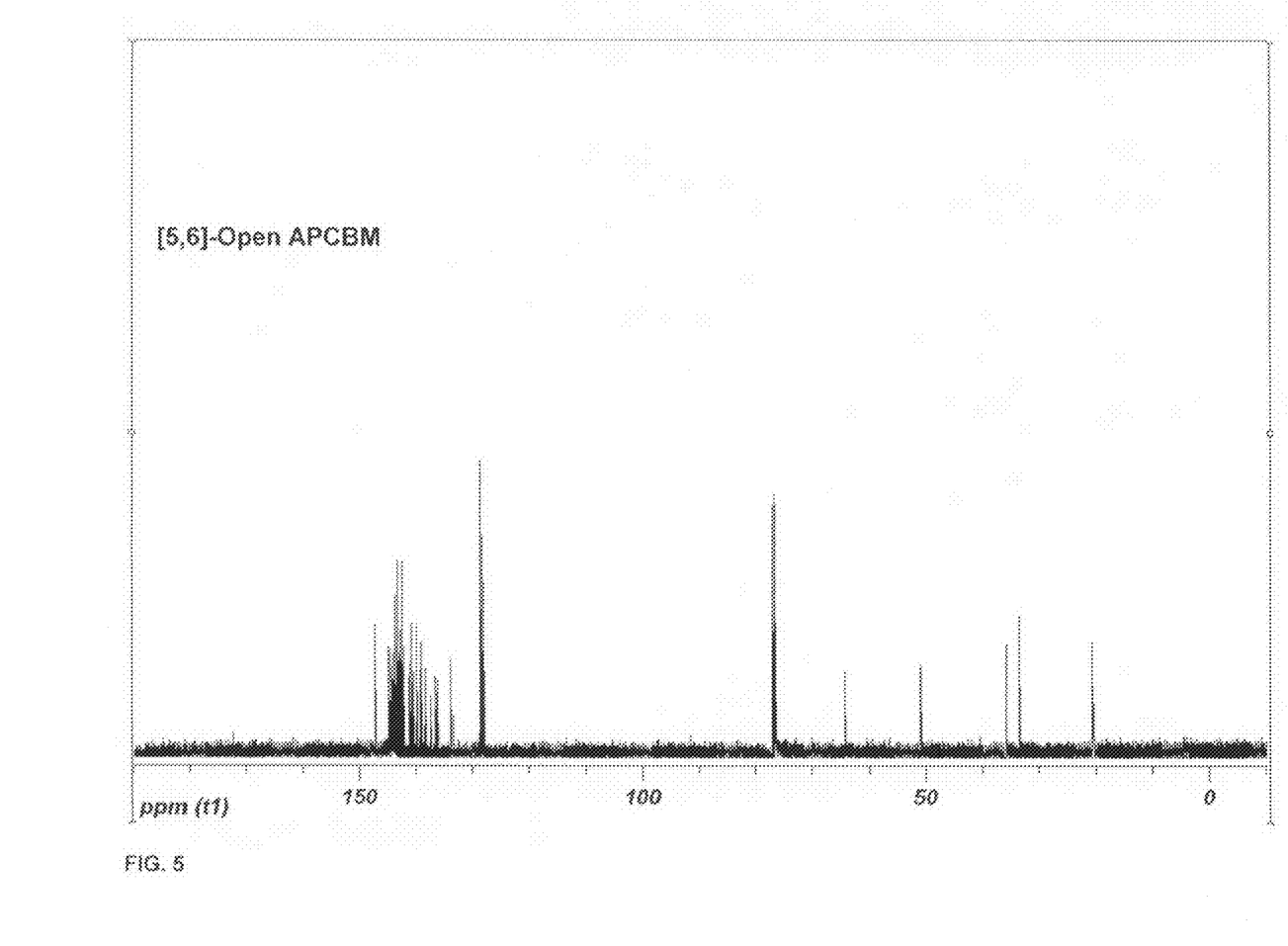
FIG. 5 is a $^{13}$C NMR spectrum of [5,6]-open APCBM.
Figure 6:
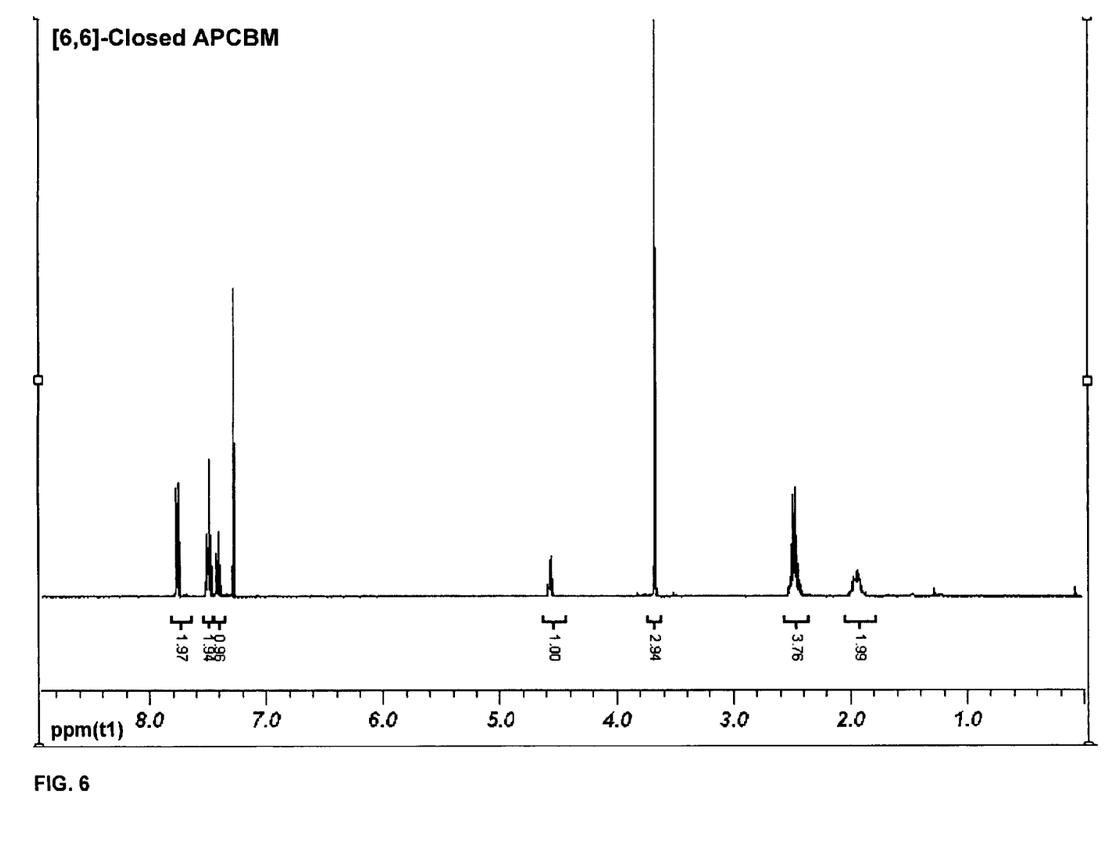
FIG. 6 is a $^1$H NMR spectrum of [6,6]-closed APCBM.
Figure 7:
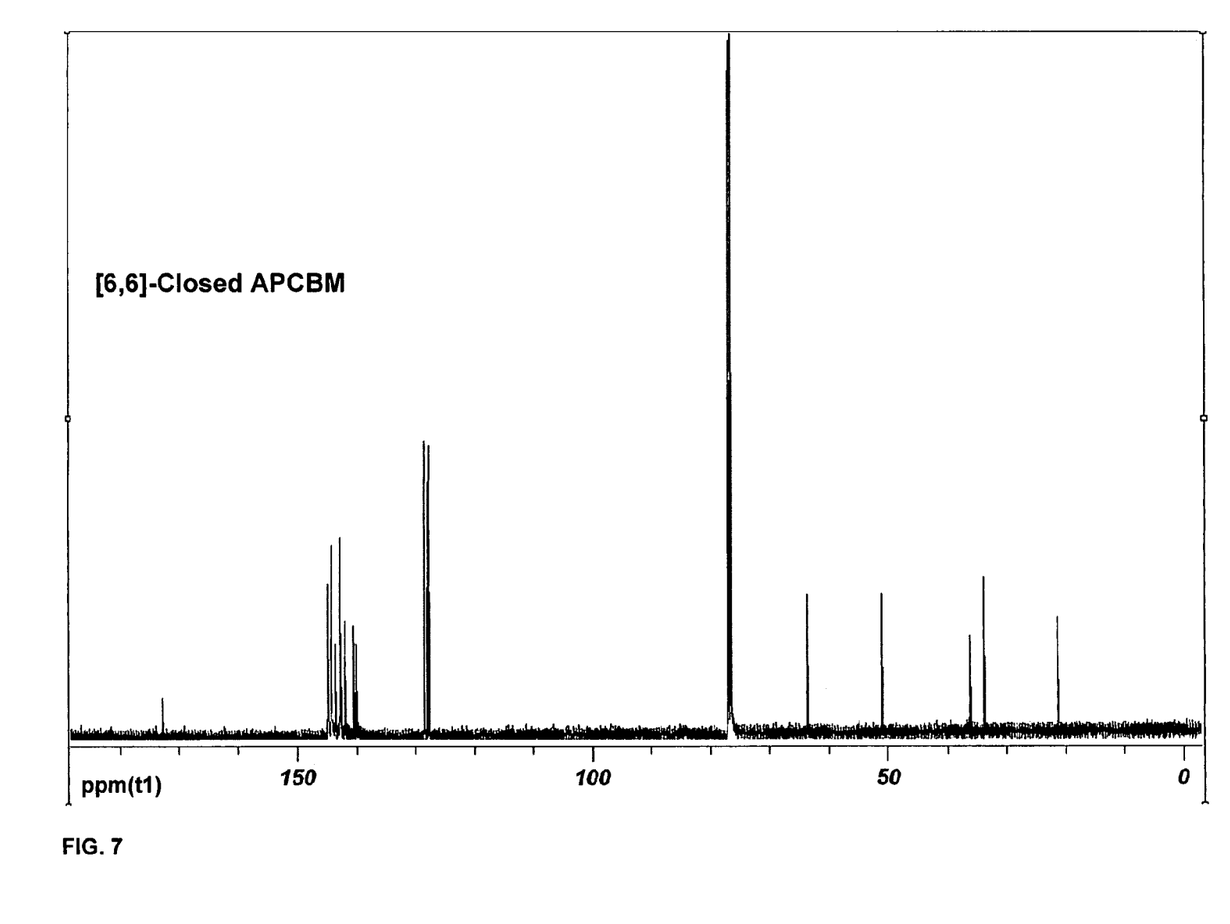
FIG. 7 is a $^{13}$C NMR spectrum of [6,6]-closed APCBM.

The imino PCBMs [5,6]-open APCBM and [6,6]-closed APCBM were prepared by thermal reaction of methyl 5-azido-5-phenylpentanoate with C$_{60}$, followed by in situ thermal N$_2$ extrusion. Column chromatography on silica gel yielded [5,6]-open APCBM as a major isomer (45% yields based on consumed C$_{60}$) and [6,6]-closed APCBM as a minor adduct (4.8%), respectively. Referring to FIG. 4, an inspection of the $^1$H NMR spectrum of [5,6]-open APCBM shows the tertiary hydrogen adjacent to the nitrogen atom as a doublet of doublets at 5.20 ppm (J=9.33 and 3.39 Hz). Also, the $^{13}$C NMR spectrum (FIG. 5) reveals that 42 signals, between 148 and 132 ppm, are attributable to the fullerene carbons. In the case of [6,6]-closed APCBM, the hydrogen α to the nitrogen atom, not only exhibits a high field shift at 4.56 ppm in the $^1$H NMR spectrum (FIG. 6), when compared to the open isomer, but also highly symmetrical 12 fullerene resonances are displayed in $^{13}$C NMR (FIG. 7).

Figure 2:
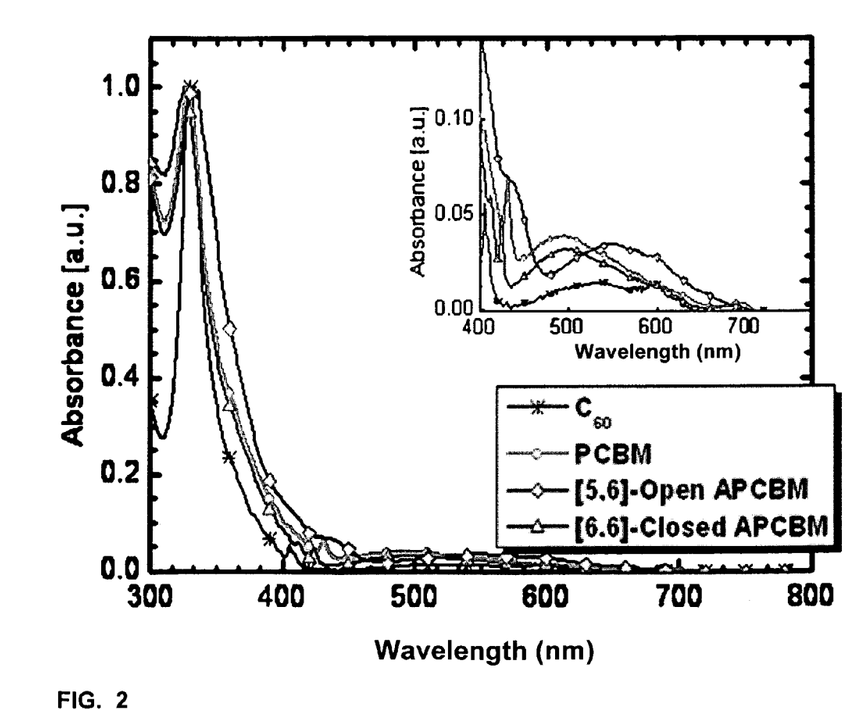
FIG. 2 is a chart showing the UV-Vis absorption of $C_{60}$, PCBM, [5,6]-open APCBM and [6,6]-closed APCBM in $CHCl_3$ solution.

FIG. 2 depicts the UV-Vis absorption characteristics of C$_{60}$, PCBM, [5,6]-open APCBM and [6,6]-closed APCBM in chloroform solution. To precisely clarify the changed features through the iminofunctionalization on C$_{60}$, the pristine C$_{60}$ and PCBM data obtained in this study are also listed in Table 1.

TABLE 1

| compound | absorption (nm) |
| --- | --- |
| C$_{60}$ | 330, 405, 540, 600, 623(sh) |
| PCBM | 328, 430, 490, 603(sh), 695 |
| [5,6]-Open APCBM | 332, 435(sh), 547, 602(sh) |
| [6,6]-Closed APCBM | 326, 423, 495, 607(sh), 685 |

The resemblance of the absorption features between PCBM and [6,6]-closed APCBM is disclosed with a distinguishable sharp band at 430 nm and 423 nm, respectively, which reflects the partially broken symmetry (C$_{2v}$) of the fullerene core, relative to pristine C$_{60}$ (I$_h$). Otherwise, the UV-Vis spectra of C$_{60}$ and [5,6]-open APCBM are almost identical in shape, exhibiting a peak at 330 nm and 332 nm and a bathochromically-shifted broad band at 540 nm and 547 nm as compared to the closed forms (PCBM and [6,6]-closed APCBM), respectively. These results are clearly suggestive that the absorption characteristics of the functionalized C$_{60}$ derivatives are governed by the changed fullerene's π-system.

Another noticeable difference in solution colors are the purple, brown, dark greenish-brown and dark wine-red color for $C_{60}$, PCBM, [5,6]-open APCBM and [6,6]-closed APCBM, respectively. This implies that the optical features of the $C_{60}$ analogues are also affected by the inductive effect of the bridged atoms in the fullerenes, i.e. the electron donating and withdrawing nature of the corresponding functionalizing addends.

Figure 8:
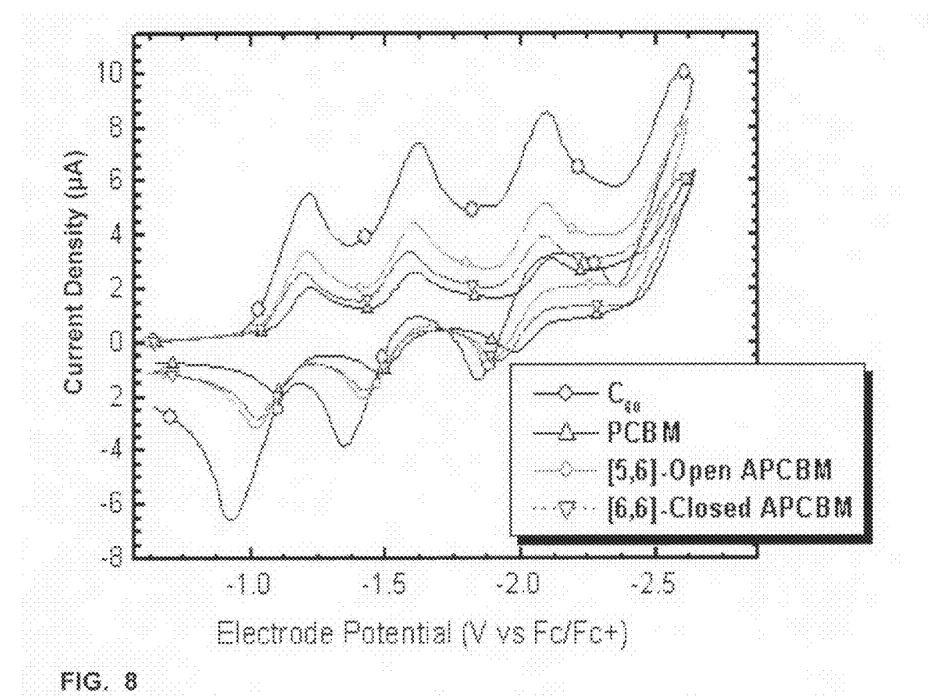
FIG. 8 are a cyclic voltammograms of $C_{60}$, PCBM, [5,6]-open APCBM and [6,6]-closed APCBM.

The electrochemical behavior of [5,6]-open APCBM and [6,6]-closed APCBM was studied by cyclic voltammetry (CV) at room temperature in ortho-dichlorobenzene (o-DCB) solution. The cyclic voltammograms of [5,6]-open APCBM and [6,6]-closed APCBM, not only show three reduction waves but also all reductions exhibit clear quasireversibility (FIG. 8). The data for all materials are summarized in Table 2.

TABLE 2

| compound | $E^1_{red}$ | $E^2_{red}$ | $E^3_{red}$ |
| --- | --- | --- | --- |
| $C_{60}$ | −1.071 | −1.484 | −1.969 |
| PCBM | −1.158 | −1.540 | −2.039 |
| [5,6]-Open APCBM | −1.114 | −1.512 | −1.984 |
| [6,6]-Closed APCBM | −1.110 | −1.504 | −2.000 |

[a]Experimental conditions: values for $0.5(E_{pa} + E_{pc})$ in V vs Fc/Fc+; $10^{-4}$ to $10^{-3}$ mol/L o-DCB solution; $Bu_4NClO_4$ (0.1M) as supporting electrolyte; Pt wire as counter electrode; 50 mV/s scan rate.

The reduction potentials of the functionalized $C_{60}$ adducts are shifted toward more negative values with respect to $C_{60}$ because of fewer π electrons and release of strain energy (25).

In the inspection of [5,6]-open APCBM and [6,6]-closed APCBM, less negative reduction values than for PCBM are observed. A likely rationale for this redox behavior is the higher electronegativity of the nitrogen atom, relative to the analogous carbon atom, resulting in slightly reduced electron density in the fullerene shell. It is also interesting to note that the reduction potentials reveal remarkable similarities between [5,6]-open APCBM and [6,6]-closed APCBM. This observation is in contrast to most all-carbon systems, in which the reduction waves of the open form occur at almost the same potential as in $C_{60}$ since they are isoelectronic analogues of $C_{60}$ (60 π-electrons) (3). These results suggest that the reduction potentials of the functionalized $C_{60}$ derivatives stem from a combination of the nature of the bridge atoms and the binding mode in fullerene framework.

It is of considerable interest to explore the differences in the properties of n-channel OFETs between the isomeric structures since this can provide an important guideline for design of $C_{60}$ derivatives for electronic applications. All n-type OFETs were fabricated on heavily doped Si wafers with a 200 nm thick $SiO_2$ layer with top contact geometry as shown in FIG. 3. To achieve easy injection of electrons without any energy barrier, Ca/Al double metal layers were used as source and drain electrodes, where the Al additional metal layer acts as a protection layer for preventing the fast oxidization of Ca.

Figure 9:
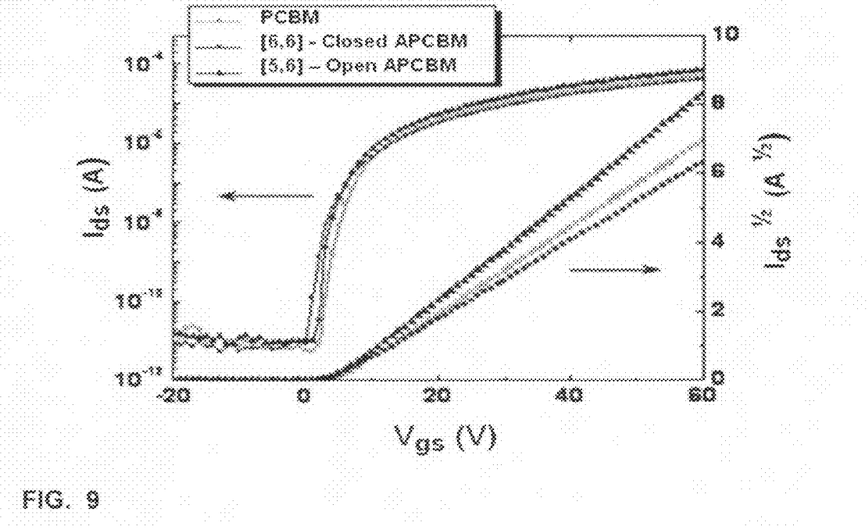
FIG. 9 is a chart showing the transfer characteristics in saturated regime (-■-; PCBM, -▲-; [5,6]-open APCBM, -●-; [6,6]-closed APCBM.
Figure 10:
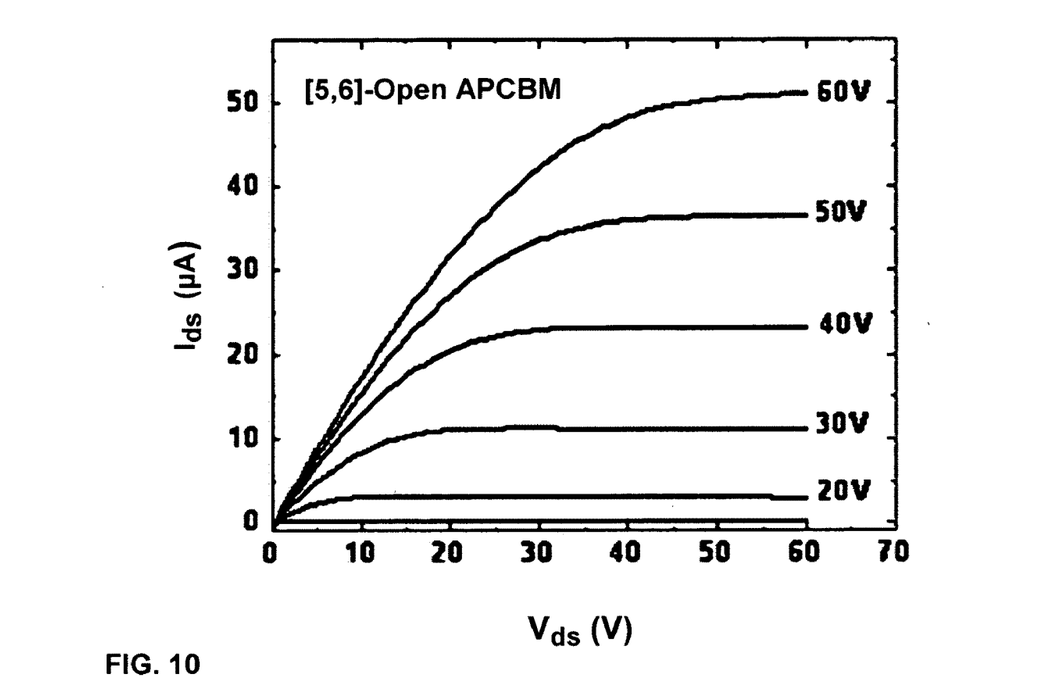
FIG. 10 is a chart showing the output curves at different gate voltages for [5,6]-open APCBM.
Figure 11:
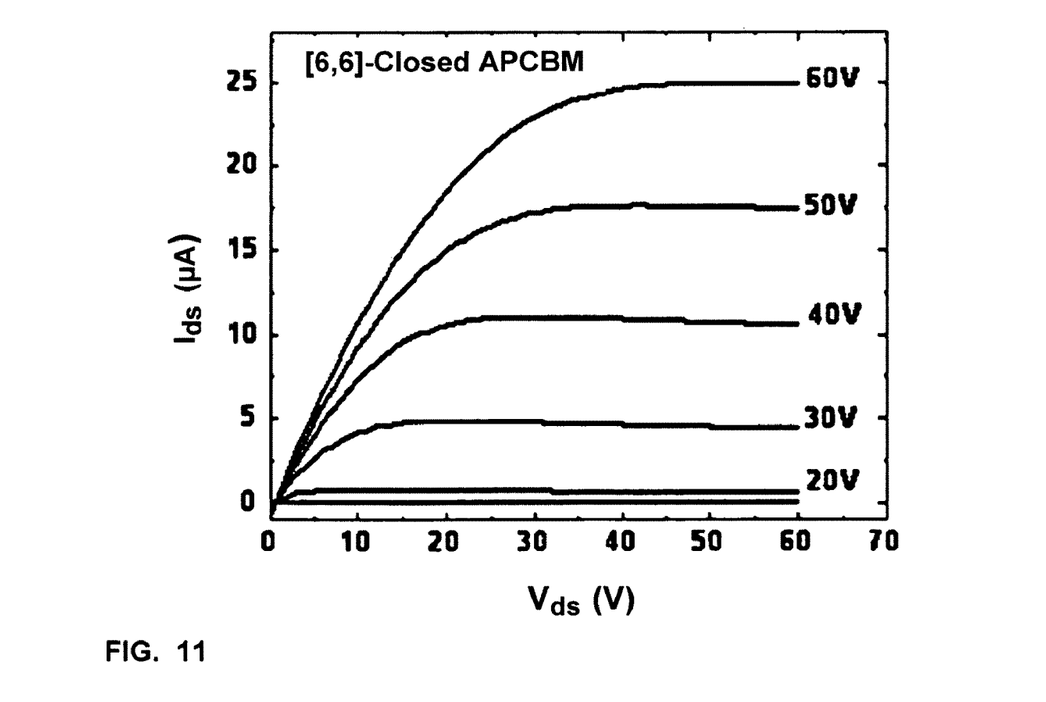
FIG. 11 is a chart showing the output curves at different gate voltages for [6,6]-closed APCBM.

As shown in FIG. 9, the transfer characteristics, $I_{ds}$ vs. $V_{gs}$ and $I_{ds}^{1/2}$ vs. $V_{gs}$ ($V_{ds}$=60 V), of the OFETs fabricated with [5,6]-open APCBM and [6,6]-closed APCBM as an active layer, respectively, are compared to the PCBM measured under identical conditions. Both [5,6]-open APCBM and [6,6]-closed APCBM reveal typical behavior of good n-type OFETs as well as excellent output characteristics with clear saturation (FIGS. 10 and 11, respectively). Notably, a non-negligible difference between [5,6]-open APCBM and [6,6]-closed APCBM in the $I_{ds}$ vs. $V_{gs}$ is observed (see the $I_{ds}^{1/2}$ vs. $V_{gs}$ plot to clearly identify), allowing the alternation of OFET performance in the output characteristic curves. The linear plot of $I_{ds}^{1/2}$ vs. $V_{gs}$ deduced from the measurements of $I_{ds}$ vs. $V_{gs}$ yields electron mobilities of $\mu_1$=4.1×10$^{-2}$ cm$^2$/V·s, $\mu_2$=2.3×10$^{-2}$ cm$^2$/V·s, $\mu_3$=2.8×10$^{-2}$ cm$^2$/V·s for [5,6]-open APCBM ($\mu_1$), [6,6]-closed APCBM ($\mu_2$), and PCBM ($\mu_3$) (the device performance was consistent in trend and reproducibility). The higher electron mobility in the [5,6]-open APCBM OFET can be attributed to the 60 π-electron nature that possesses stronger electron acceptor strength than that of the [6,6]-junctions (26). On the other hand, the mobility value of the [6,6]-closed APCBM reveals an obvious similarity to the isoelectronic isomer PCBM. These results are indicative that the nature of the bridged heteroatom may not engage with the n-type electronic properties of $C_{60}$ but a perturbation of the fullerene's π-electrons can, indeed, tune the electron transfer characters that can be responsible for the variation of the mobilities in OFETs.

Two isomeric stable imino PCBMs ([5,6]-open APCBM and [6,6]-closed APCBM) were prepared. The former isomer retains the intact π-electron system of the parent $C_{60}$, whereas the fullerene core of the latter reflects a loss 2 π-electrons, which results in a difference of their electron accepting properties. As a result, of particular significance is that the n-channel OFET with [5,6]-open APCBM, in a solution processed device, exhibits a substantial electron mobility ($\mu$=4.1×10$^{-2}$ cm$^2$/V·s), which is the first example of a fullerene with mobility that exceeds that of the optimized high performance of PCBM ($\mu$=2.8×10$^{-2}$ cm$^2$/V·s).

REFERENCES

1. Thilgen, C.; Diederich, F. Chem. Rev. 2006, 106, 5049.
2. Janssen, R. A. J.; Hummelen, J. C.; Wudl, F. J. Am. Chem. Soc. 1995, 117, 544.
3. Hummelen, J. C.; Knight, B. W.; Lepeq, F.; Wudl, F.; Yao, J.; Wilkins, C. L. J. Org. Chem. 1995, 60, 532.
4. Maggini, M.; Scorrano, G.; Bianco, A.; Toniolo, C.; Sijbesma, R. P.; Wudl, F.; Prato, M. J. Chem. Soc., Chem. Commun. 1994, 305.
5. Hirsch, A. The Chemistry of the Fullerenes; Thieme: Stuttgart, 1994.
6. Taylor, R.; Walton, D. R. M. Nature 1993, 363, 685.
7. Rubin, Y.; Khan, S.; Freedberg, D. I.; Yeretzian, C. J. Am. Chem. Soc. 1993, 115, 344.
8. Prato, M.; Suzuki, T.; Foroudian, H.; Li, Q.; Khemani, K.; Wudl, F.; Leonetti, J.; Little, R. D.; White, T.; Rickborn, B.; Yamago, S.; Nakamura, E. J. Am. Chem. Soc. 1993, 115, 1594.
9. Meier, M. S.; Poplawska, M. J. Org. Chem. 1993, 58, 4524.
10. Komatsu, K.; Kagayama, A.; Murata, Y.; Sugita, N.; Kobayashi, K.; Nagase, S.; Wan, T. S. M. Chem. Lett. 1993, 2163.
11. Wudl, F. Acc. Chem. Res. 1992, 25, 157.
12. Wudl, F. In Fullerenes Synthesis, Properties, and Chemistry of Large Carbon Clusters; Hammond, G. S., Kuck, V. J., Eds.; American Chemistry Society: Washington, D.C., 1992; Vol. 481, p 161.
13. Vasella, A.; Uhlmann, P.; Waldraff, C. A. A.; Diederich, F.; Thilgen, C. Angew. Chem., Int. Ed. Engl. 1992, 31, 1388.
14. Paolucci, F.; Marcaccio, M.; Roffia, S.; Orlandi, G.; Zerbetto, F.; Prato, M.; Maggini, M.; Scorrano, G. J. Am. Chem. Soc. 1995, 117, 6572.
15. Eiermann, M.; Wudl, F.; Prato, M.; Maggini, M. J. Am. Chem. Soc. 1994, 116, 8364.
16. Diederich, F.; Isaacs, L.; Philp, D. Chem. Soc. Rev. 1994, 23, 243.
17. Cases, M.; Duran, M.; Mestres, J.; Martin, N.; Solà, M. J. Org. Chem. 2001, 66, 433.

18. Grösser, T.; Prato, M.; Lucchini, V.; Hirsch, A.; Wudl, F. Angew. Chem., Int. Ed. Engl. 1995, 34, 1343.
19. Prato, M.; Li, Q. C.; Wudl, F.; Lucchini, V. J. Am. Chem. Soc. 1993, 115, 1148.
20. Guldi, D. M.; Hungerbühler, H.; Carmichael, I.; Asmus, K. D.; Maggini, M. J. Phys. Chem. A 2000, 104, 8601.
21. Hirsch, A. In Fullerenes and Related Structures 1999; Vol. 199, p 1.
22. Averdung, J.; Tones-Garcia, G.; Luftmann, H.; Schlachter, I.; Mattay, J. Full. Sci. Techn. 1996, 4, 633.
23. Averdung, J.; Mattay, J. Tetrahedron 1996, 52, 5407.
24. Benati, L.; Leardini, R.; Minozzi, M.; Nanni, D.; Spagnolo, P.; Strazzari, S.; Zanardi, G. Org. Lett. 2002, 4, 3079.
25. Haddon, R. C. Science 1993, 261, 1545.
26. Brabec, C. J.; Cravino, A.; Meissner, D.; Sariciftci, N. S.; Fromherz, T.; Rispens, M. T.; Sanchez, L.; Hummelen, J. C. Adv. Funct. Mater. 2001, 11, 374.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

What is claimed is:

1. An imino PCBM selected from the group consisting of [5,6]-open APCBM, [6,6]-closed APCBM, and an isomeric mixture thereof.

2. An organic electronic device comprising an imino PCBM of claim 1.

3. The organic electronic device of claim 2, wherein the imino PCBM has an electron mobility that is greater than the electron mobility of PCBM when measured under similar conditions.

4. The organic electronic device of claim 2, wherein the organic electronic device is an organic field effect transistor.

* * * * *